United States Patent [19]

Rentzea et al.

[11] Patent Number: 4,684,392

[45] Date of Patent: Aug. 4, 1987

[54] BETA-TRIAZOLYL OXIMES AGENTS CONTAINING THEM FOR INFLUENCING THE GROWTH OF PLANTS AND THEIR USE

[75] Inventors: Costin Rentzea, Heidelberg; Hubert Sauter; Bernd Zeeh, both of Ludwigshafen; Gerd Heilen, Speyer; Johann Jung, Limburgerhof, all of Fed. Rep. of Germany

[73] Assignee: BASF Aktiengesellschaft, Ludwigshafen, Fed. Rep. of Germany

[21] Appl. No.: 690,367

[22] Filed: Jan. 9, 1985

Related U.S. Application Data

[63] Continuation of Ser. No. 414,171, Sep. 2, 1982, abandoned, which is a continuation of Ser. No. 76,781, Sep. 18, 1979, abandoned.

[30] Foreign Application Priority Data

Sep. 30, 1978 [DE] Fed. Rep. of Germany ....... 2842801

[51] Int. Cl.$^4$ .................. A01N 43/653; C07D 249/08
[52] U.S. Cl. ............................................ 71/76; 71/90; 71/92; 548/262
[58] Field of Search ..................... 548/262; 71/76, 90, 71/92

[56] References Cited

U.S. PATENT DOCUMENTS

| | | | |
|---|---|---|---|
| 4,113,465 | 9/1978 | Shephard et al. | 71/92 |
| 4,124,767 | 11/1978 | Mixich et al. | 424/273 R |
| 4,344,953 | 8/1982 | Stetter et al. | 424/269 |
| 4,357,338 | 11/1982 | Kramer et al. | 424/269 |
| 4,360,526 | 11/1982 | Zeeh et al. | 424/245 |

FOREIGN PATENT DOCUMENTS

| | | | |
|---|---|---|---|
| 2634511 | 2/1978 | Fed. Rep. of Germany | 548/262 |
| 2805227 | 8/1978 | Fed. Rep. of Germany | 548/262 |

*Primary Examiner*—Richard L. Raymond
*Assistant Examiner*—D. Dinner
*Attorney, Agent, or Firm*—Keil & Weinkauf

[57] ABSTRACT

New substituted β-triazolyl oximes, processes for their manufacture, agents for regulating plant growth containing these compounds, and a process for regulating plant growth with these compounds.

2 Claims, No Drawings

BETA-TRIAZOLYL OXIMES AGENTS CONTAINING THEM FOR INFLUENCING THE GROWTH OF PLANTS AND THEIR USE

This application is a continuation of application Ser. No. 414,171, filed on Sept. 2, 1982 which is a continuation of Ser. No. 076,781 filed Sept. 18, 1979, now all abandoned.

The present invention relates to new and valuable substituted β-triazolyl oximes, processes for their manufacture, agents for regulating plant growth containing these compounds, and a process for regulating plant growth with these compounds.

The use of 2-choroethyltrimethylammonium chloride (chlorocholine chloride, CCC) for influencing plant growth has been disclosed (J. Biol. Chem., 235, 475, 1960). It helps for instance to reduce growth height in some cereal species and to inhibit vegetative growth in some other crop plants. However, the action of this compound, particularly at low application rates, is not always sufficient and does not always meet the requirements of practice.

The use of 1-(4'-bromophenyl)-1-allyloxy-2-(1",2",4"-triazolyl-(1"))-ethane for regulating growth in rape, wheat, oats, rye and barley has also been disclosed (German Laid-Open Application DE-OS No. 2,650,831). However, its action, particularly at low application rates, is not always satisfactory.

We have now found that compounds of the formula

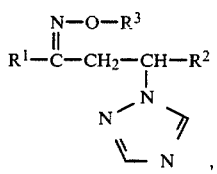   I where $R^1$ and $R^2$ are identical or different and each denotes alkyl of 1 to 6 carbon atoms, furanyl, thiophenyl, naphthyl, biphenylyl or phenyl, phenyl being unsubstituted or substituted by fluoro, chloro, bromo, alkyl of 1 to 4 carbon atoms, trifluoromethyl, nitro, or by alkoxy of 1 to 4 carbon atoms, and $R^3$ denotes hydrogen, alkyl of 1 to 4 carbon atoms, alkenyl of 1 to 4 carbon atoms, unsubstituted or substituted benzyl, —CO—$R^4$, $R^4$ denoting alkyl of 1 to 4 carbon atoms which is unsubstituted or halogen- or alkoxy-substituted, or an aromatic radical, or $R^3$ denotes —CO—NH—$R^5$, $R^5$ denoting alkyl of 1 to 4 carbon atoms or an aromatic radical, are excellently suited for regulating plant growth and are excellently tolerated by crop plants.

Sterically, the new compounds of the formula I may be in the Z- or the E-form. Usually, mixtures predominate.

We have further found that β-triazolyl oximes of the formula I are obtained by reacting a β-triazole oxime of the formula ($R^3$=H)

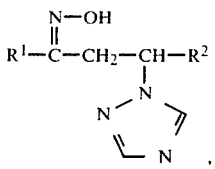

where $R^1$ and $R^2$ have the above meanings, with an alkyl, alkenyl or benzyl halide of the formula

   II where $R^3$ has the above meanings and X denotes chlorine or bromine, or with an acid chloride or acid anhydride of the formula

   III where $R^4$ has the above meanings and Y denotes chlorine, bromine or —O—CO—$R^4$, or with an isocyanate of the formula

   IV or with a carbamoyl chloride of the formula

   V $R^5$ having the above meanings, in the presence or absence of a basic catalyst and in the presence or absence of a diluent.

Further, we have found that compounds of the formula I are obtained by reaction of a β-triazolyl ketone of the formula

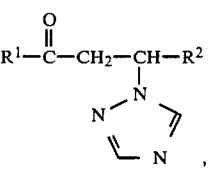   VI where $R^1$ and $R^2$ have the above meanings, with a hydroxylamine derivative of the formula

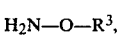   VII where $R^3$ denotes hydrogen, alkyl of 1 to 4 carbon atoms, alkenyl of 1 to 4 carbon atoms, or benzyl, in the presence or absence of a basic or acid catalyst and in the presence or absence of a diluent. This method is preferred.

In the formulae, $R^1$ and $R^2$, which may be identical or different, denote for example methyl, propyl, n-butyl, sec-butyl, isobutyl, tert-butyl, n-pentyl, neopentyl, hexyl, furanyl, thiophenyl, naphthyl, biphenylyl, phenyl, m- and p-tolyl, p-tert-butylphenyl, o- and p-methoxyphenyl, 2,4-dimethoxyphenyl, p-fluorophenyl, o- and p-chlorophenyl, p-bromophenyl, 2,4-dichlorophenyl, p-nitrophenyl, and p-trifluoromethylphenyl.

Compounds of the formula VI are disclosed in German Laid-Open Application DE-OS 2,634,511 and may readily be prepared by the processes described therein.

The alkyl, alkenyl and benzyl halides of the formula II, the acid chlorides and acid anhydrides of the formula III, the alkyl and aryl isocyanates of the formula IV, the carbamoyl chlorides of the formula V, and the hydroxylamines of the formula VII are known and may readily be prepared by conventional processes.

The β-triazolyl ketones of the formula VI are advantageously reacted with starting materials of the formula VII in water or a water-miscible solvent. Examples are alcohols, such as methanol, ethanol, propanol, ethylene glycol, and 2-methoxyethanol; ethers, such as tetrahydrofuran and dioxane; amides, such as dimethylformamide, diethylformamide, and dimethyl acetamide, further N-methylpyrrolidone and hexamethylphosphoric acid, and acids such as formic acid, acetic acid and propionic acid. It is advantageous to add a base, such as for example sodium hydroxide, potassium hydroxide, barium hydroxide or sodium acetate, an amine, such as triethylamine, piperidine or N-methylpiperidine, or an acid, such as hydrochloric acid, sulfuric acid, phosphoric acid, formic acid or acetic acid.

The reaction temperature may vary within a wide range; it is generally from 0° to 70° C., and preferably from 0° to 40° C.

The reaction of β-azolyl oximes of the formula I ($R^3$=H) with starting materials of the formulae II, III, IV and V is advantageously carried out without a diluent, or in an inert solvent. Examples are acetonitrile; ethers, such as diethyl ether, dipropyl ether, dibutyl ether, tetrahydrofuran, dioxane, and dimethoxyethane; esters, such as ethyl acetate; ketones, such as acetone and methyl ethyl ketone; chlorinated hydrocarbons, such as methylene chloride, chloroform, carbon tetrachloride, dichloroethane, tetrachloroethane, and chlorobenzene; and hydrocarbons, such as benzene, toluene, and xylene. It is advantageous to add, as auxiliary base or in catalytic amounts, a base such as, for example, sodium carbonate, potassium carbonate, calcium carbonate, and sodium acetate, or an amine, such as triethylamine, pyridine, imidazole, or piperidine. The reaction temperature may vary from −25° to +100° C., and is preferably from +10° to +80° C.

The compounds of the formula I which are thus obtained are isolated by conventional methods and, if desired, purified.

The following compounds are examples of particularly effective representatives of the new active ingredients:

4-(1',2',4'-triazolyl-(1'))-5,5-dimethylhexan-2-one oxime,
3-(1',2',4'-triazolyl-(1'))-2,2-dimethyloctan-5-one oxime,
3-(1',2),4'-triazolyl-(1'))-2,2-dimethylnonan-5-one oxime,
3-(1',2',4'-triazolyl-(1'))-2,2-dimethyldecan-5-one oxime,
3-(1',2',4'-triazolyl-(1'))-2,2-dimethylundecan-5-one oxime,
3-(1',2',4'-triazolyl-(1'))-1-phenyl-4,4-dimethylpentan-1-one oxime,
3-(1',2',4'-triazolyl-(1'))-1-(4''-fluorophenyl)-4,4-dimethylpentan-1-one oxime,
3-(1',2',4'-triazolyl-(1'))-1-(4''-fluorophenyl)-4,4-dimethylpentan-1-one-O-methyl oxime,
3-(1',2',4'-triazolyl-(1'))-1-(4''-chlorophenyl)-4,4-dimethylpentan-1-one oxime,
3-(1',2',4'-triazolyl-(1'))-1-(4''-chlorophenyl)-4,4-dimethylpentan-1-one-O-acetyl oxime,
3-(1',2',4'-triazolyl-(1'))-1-(4''-chlorophenyl)-4,4-dimethylpentan-1-one-O-propionyl oxime,
3-(1',2',4'-triazolyl-(1'))-1-(4''-bromophenyl)-4,4-dimethylpentan-1-one oxime,
3-(1',2',4'-triazolyl-(1'))-1-(4''-bromophenyl)-4,4-dimethylpentan-1-one-O-acetyl oxime,
3-(1',2',4'-triazolyl-(1'))-1-(4''-bromophenyl)-4,4-dimethylpentan-1-one-O-propionyl oxime,
3-(1',2',4'-triazolyl-(1'))-1-(2'',4''-dichlorophenyl)-4,4-dimethylpentan-1-one oxime,
3-(1',2',4'-triazolyl-(1'))-1-(4''-tolyl)-4,4-dimethylpentan-1-one oxime,
3-(1',2',4'-triazolyl-(1'))-1-(3''-tolyl)-4,4-dimethylpentan-1-one oxime,
3-(1',2',4'-triazolyl-(1'))-1-(4''-methoxyphenyl)-4,4-dimethylpentan-1-one oxime,
1-(1',2',4'-triazolyl-(1'))-1-(4''-chlorophenyl)-5,5-dimethylhexan-3-one oxime,
3-(1',2',4'-triazolyl-(1'))-1-(4''-biphenylyl)-4,4-dimethylpentan-1-one oxime,
3-(1',2',4'-triazolyl-(1'))-1-(2''-furfuryl)-4,4-dimethylpentan-1-one oxime,
3-(1',2',4'-triazolyl-(1'))-1-(2''-thiophenyl)-4,4-dimethylpentan-1-one oxime,
3-(1',2',4'-triazolyl-(1'))-1,3-diphenylpropan-1-one oxime,
3-(1',2',4'-triazolyl-(1'))-1,3-diphenylpropan-1-one O-acetyl oxime,
3-(1',2',4'-triazolyl-(1'))-1,3-diphenylpropan-1-one-O-(methylcarbamoyl)-oxime,
3-(1',2',4'-triazolyl-(1'))-1,3-diphenylpropan-1-one-O-(p-chlorophenylcarbamoyl)-oxime,
3-(1',2',4'-triazolyl-(1'))-1-phenyl-3-(4''-tolyl)-propan-1-one oxime,
3-(1',2',4'-triazolyl-(1'))-1-phenyl-3-(4''-methoxyphenyl)-propan-1-one oxime,
3-(1',2',4'-triazolyl-(1'))-1-phenyl-3-(4''-tert-butylphenyl)-propan-1-one oxime,
3-(1',2',4'-triazolyl-(1'))-1-phenyl-3-(4''-nitrophenyl)-propan-1-one oxime,
3-(1',2',4'-triazolyl-(1'))-1-phenyl-3-(1''-naphthyl)-propan-1-one oxime,
3-(1',2',4'-triazolyl-(1'))-1-(4''-trifluoromethylphenyl)-3-phenylpropan-1-one oxime,
3-(1',2',4'-triazolyl-(1'))-(4''-chlorophenyl)-3-(4''-tolyl)-propan-1-one oxime,
3-(1',2',4'-triazolyl-(1'))-1-(2''-methoxyphenyl)-3-(4''-chlorophenyl)-propan-1-one oxime,
3-(1',2',4'-triazolyl-(1'))-1-phenyl-4,4-dimethylpentan-1-one-O-methyl oxime,
3-(1',2',4'-triazolyl-(1'))-1-phenyl-4,4-dimethylpentan-1-one-O-allyl oxime,
3-(1',2',4'-triazolyl-(1'))-1-(4''-chlorophenyl)-4,4-pentan-1-one-O-methyl oxime,
3-(1',2',4'-triazolyl-(1'))-1-(4''-chlorophenyl)-4,4-pentan-1-one-O-allyl oxime,
3-(1',2',4'-triazolyl-(1'))-1-(4''-chlorophenyl)-4,4-pentan-1-one-O-benzoyl oxime,
3-(1',2',4'-triazolyl-(1'))-1-(4''-bromophenyl)-4,4-pentan-1-one-O-methyl oxime,
3-(1',2',4'-triazolyl-(1'))-1-(4''-bromophenyl)-4,4-pentan-1-one-O-allyl oxime, and
3-(1',2',4'-triazolyl-(1'))-1-(4''-bromophenyl)-3,3-pentan-1-one-O-benzyl oxime.

The following examples illustrate the manufacture of the new compounds.

EXAMPLE 1

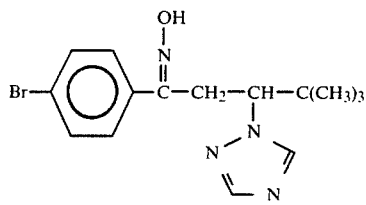

While stirring thoroughly, 9.7 g of hydroxylamine hydrochloride is introduced into a solution of 33.6 g of 3-(1',2',4'-triazolyl-(1'))-1-(4''-bromophenyl)-4,4-dimethylpentan-1-one in 100 ml of ethanol. After the mixture has been stirred for 24 hours at room temperature it is concentrated. 250 ml of methylene chloride and subsequently 200 ml of a 5% strength (by weight) aqueous sodium bicarbonate solution are added to the residue, and the mixture is stirred for 10 minutes. The organic layer is dried over $Na_2SO_4$ and concentrated in vacuo. The colorless crystalline residue which remains is washed with 100 ml of petroleum ether and filtered. There is obtained 30.2 g (86.1% of theory) of 3-(1',2',4'-triazolyl-(1'))-1-(4''-bromophenyl)-4,4-dimethylpentan-1-one oxime of melting point 185° to 186° C. (active ingredient no. 1).

EXAMPLE 2

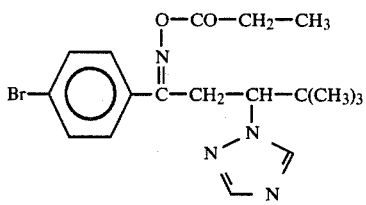

17 g of 3-(1',2',4'-triazolyl-(1'))-1-(4''-bromophenyl)-4,4-dimethylpentan-1-one oxime and 0.5 g of imidazole are dissolved in 60 g of propionic anhydride, and the mixture is stirred for 6 hours at 45° C. The solvent is then distilled off in vacuo, 200 ml of methylene chloride and subsequently 150 ml of a 5% strength sodium bicarbonate solution are added to the residue, and the mixture is stirred for 30 minutes. The organic phase is then washed twice, each time with 100 ml of water, dried over $Na_2SO_4$, filtered and concentrated. The residue is washed with 100 ml of petroleum ether, filtered and dried.

There is obtained 16.3 g (83% of theory) of 3-(1',2',4'-triazolyl-(1'))-1-(4''-bromophenyl)-4,4-dimethylpentan-1-one-O-propionyl oxime as white crystals which analyze pure; melting point: 106° to 108° C. (active ingredient no. 2).

EXAMPLE 3

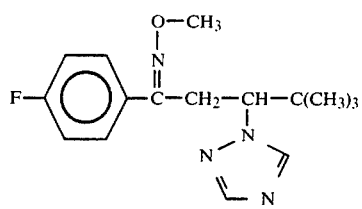

While stirring well, 11.6 g of O-methylhydroxylamine hydrochloride and 14.1 g of triethylamine are introduced into a solution of 28.7 g of 3-(1',2',4'-triazolyl-(1'))-1-(4''-fluorophenyl)-4,4-dimethylpentan-1-one in 100 ml of methanol. After the mixture has been stirred for 2 hours at 50° C., it is concentrated. The residue is extracted with 250 ml of methylene chloride and 200 ml of water. The organic phase is dried over sodium sulfate and concentrated in vacuo. The solid colorless residue which remains is digested with 80 ml of diethyl ether for 2 hours at −5° C., filtered, washed with a small amount of cold ether, and dried.

There is obtained 14 g (46% of theory) of 3-(1',2',4'-triazolyl-(1'))-1-(4''-fluorophenyl)-4,4-dimethylpentan-1-one-O-methyl oxime as white crystals; m.p.: 109° to 111° C. (active ingredient no. 3).

EXAMPLE 4

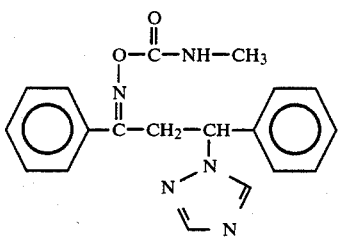

While stirring well, 8.5 g of methyl isocyanate is dripped, at room temperature and over a period of 10 minutes, into a solution of 29.2 g of 3-(1',2',4'-triazolyl-(1'))-1,3-diphenylpropan-1-one oxime and 0.5 g of triethylamine in 150 ml of anhydrous dioxane.

After the mixture has been stirred for 8 hours at 40° C. it is concentrated. The solid, colorless residue is stirred with 50 ml of diethyl ether at 0° C., filtered and dried. There is obtained 28.3 g (81% of theory) of 3-(1',2',4'-triazolyl-(1'))-1,3-diphenylpropan-1-one-O-(methylcarbamoyl)-oxime as white crystals; m.p.: 105° to 108° C. (active ingredient no. 4).

The compounds listed in Table 1 below may be prepared analogously.

TABLE 1
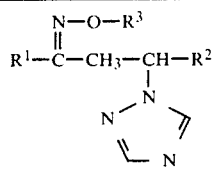
| Active ingredient no. | R¹ | R² | R³ | m.p. °C. |
|---|---|---|---|---|
| 5 | CH₃—(CH₃)₂— | —C(CH₃)₃ | H | 141–143 |
| 6 | CH₃—(CH₂)₃— | —CH(CH₃)₂ | H | 73–76 |
| 7 | CH₃—(CH₂)₃— | —C(CH₃)₃ | H | 152–154 |
| 8 | CH₃—(CH₂)₄— | —C(CH₃)₃ | H E-form | 141–143 |
|   |   |   | Z-form | 81–83 |
| 9 | C₆H₅— | —C(CH₃)₃ | H | 168–170 |
| 10 | F—C₆H₄— | —C(CH₃)₃ | H | 167–169 |
| 11 | Cl—C₆H₄— | —C(CH₃)₃ | H | 170–172 |
| 12 | (CH₃)₃C—CH₂— | Cl—C₆H₄— | H | 136–138 |
| 13 | Br—C₆H₄— | —C(CH₃)₃ | CH₃—CO— | 128–130 |
| 14 | 2,4-Cl₂—C₆H₃— | —C(CH₃)₃ | H | 202–205 |
| 15 | H₃C—C₆H₄— | —C(CH₃)₃ | H | 178–180 |
| 16 | 3,5-(H₃C)₂—C₆H₃— | —C(CH₃)₃ | H | 149–151 |
| 17 | CH₃—O—C₆H₄— | —C(CH₃)₃ | H | 174–176 |
| 18 | C₆H₅—C₆H₄— | C(CH₃)₃ | H | 180–183 |
| 19 | furyl | —C(CH₃)₃ | H | 159–160 |

TABLE 1-continued $$\begin{array}{c} N-O-R^3 \\ \| \\ R^1-C-CH_2-CH-R^2 \\ | \\ \text{triazole} \end{array}$$

| Active ingredient no. | R¹ | R² | R³ | m.p. °C. |
|---|---|---|---|---|
| 20 | 2-thienyl | —C(CH₃)₃ | H | 139–142 |
| 21 | C₆H₅— | C₆H₅ | H | 153–156 |
| 22 | C₆H₅— | C₆H₅— | CH₃—CO— | 100–101 |
| 23 | C₆H₅— | 4-CH₃-C₆H₄— | H | 181–185 |
| 24 | C₆H₅— | 4-CH₃O-C₆H₄— | H | 132–134 |
| 25 | 4-Cl-C₆H₄— | 2-OCH₃-C₆H₄— | H | 185–186 |
| 26 | C₆H₅— | 4-(CH₃)₃C-C₆H₄— | H | 149–151 |
| 27 | C₆H₅— | 4-O₂N-C₆H₄— | H | 194–196 |
| 28 | C₆H₅— | naphthyl | H | 173–175 |
| 29 | 4-F₃C-C₆H₄— | C₆H₅ | H | 206–208 |
| 30 | 4-Cl-C₆H₄— | 4-CH₃-C₆H₄— | H | 211–213 |
| 31 | C₆H₅— | (CH₃)₃C— | CH₃—CO— | 131–133 |
| 32 | C₆H₅— | (CH₃)₃C— | CH₃CH₂CO— | 60–62 |
| 33 | C₆H₅ | (CH₃)₃C— | C₆H₅—CO— | 137–139 |
| 34 | 4-F-C₆H₄— | (CH₃)₃C— | CH₃—CO— | 132–134 |

TABLE 1-continued $$\underset{R^1-C-CH_3-CH-R^2}{\overset{N-O-R^3}{\|}}$$
(with 1,2,4-triazol-1-yl on CH)

| Active ingredient no. | R¹ | R² | R³ | m.p. °C. |
|---|---|---|---|---|
| 35 | 4-F-C₆H₄— | (CH₃)₃C— | CH₃CH₂CO— | 104–106 |
| 36 | 4-F-C₆H₄— | (CH₃)₃C— | C₆H₅—CO— | 155–157 |
| 37 | 4-Cl-C₆H₄— | (CH₃)₃C— | CH₃—CO— | 123–126 |
| 38 | 4-Cl-C₆H₄— | (CH₃)₃C— | CH₃CH₂CO— | 102–104 |
| 39 | 4-Cl-C₆H₄— | (CH₃)₃C— | (CH₃)₂CHCH₂CO— | 98–100 |
| 40 | (CH₃)₃C—CH₂— | 4-Cl-C₆H₄— | CH₃CO— | 108–110 |
| 41 | 4-CH₃O-C₆H₄— | (CH₃)₃CO— | CH₃—C— | 119–121 |
| 42 | 4-CH₃O-C₆H₄— | (CH₃)₃C— | CH₃CH₂CO— | 99–101 |
| 43 | 4-CH₃O-C₆H₄— | (CH₃)₃C— | C₆H₅—CO— | 121–123 |
| 44 | 4-C₂H₅O-C₆H₄— | (CH₃)₃C— | H | 165–168 |
| 45 | 4-C₂H₅O-C₆H₄— | (CH₃)₃C— | CH₃—CO— | 111–113 |

TABLE 1-continued $$R^1-\underset{\underset{\underset{\underset{N}{\diagdown}\diagup\nearrow}{N}}{|}}{\overset{\overset{N-O-R^3}{\|}}{C}}-CH_3-CH-R^2$$

| Active ingredient no. | R¹ | R² | R³ | m.p. °C. |
|---|---|---|---|---|
| 46 | n-C₃H₇—O—⟨C₆H₄⟩— | (CH₃)₃C— | H | 150–152 |
| 47 | n-C₃H₇—O—⟨C₆H₄⟩— | (CH₃)₃C— | CH₃—CO— | 97–99 |
| 48 | n-C₃H₇—O—⟨C₆H₄⟩— | (CH₃)₃C— | CH₃CH₂CO— | 81–83 |
| 49 | n-C₄H₉—O—⟨C₆H₄⟩— | (CH₃)₃C— | H | 149–151 |
| 50 | n-C₄H₉—O—⟨C₆H₄⟩— | (CH₃)₃C— | CH₃CO— | 119–121 |
| 51 | n-C₄H₉—O—⟨C₆H₄⟩— | (CH₃)₃C— | CH₃CH₂CO— | 70–71 |
| 52 | C₆H₅— | naphthyl | CH₃—CO— | resin |
| 53 | C₆H₅— | naphthyl | CH₃CH₂CO— | resin |

The new compounds may influence practically all development stages of a plant in different ways. They are therefore used as plant growth regulators.

The diversity of action of growth regulators depends especially on (a) the type and variety of plant;
(b) the time applied, with reference to the development stage of the plants and the time of year;
(c) the place and method of application (seed treatment, soil treatment, or application to leaves);
(d) climatic factors (sunshine duration, average temperature, precipitate);
(e) soil conditions (including fertilization);
(f) the formulation or application form of the active ingredient; and
(g) the concentration at which the active ingredient is applied.

A description of some of the various possibilities of using growth regulators in agriculture and horticulture is given below.

A. With the compounds according to the invention, vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embankments and on areas such as parks, sportsgrounds, and fruit orchards, lawns and airfields, thus reducing expensive and time-consuming mowing.

A further feature of economic interest is the increase in the rigor of crops which tend to lodge, such as cereals, Indian corn and soybeans. The shortening and strengthening of the stem thus caused reduces or eliminates the danger of lodging under unfavorable weather conditions.

The use of growth regulators is also important for reducing plant height and changing the time of ripening in cotton. It is thus possible for this important crop to be harvested completely mechanically.

Growth regulators may also increase or inhibit lateral branching. This is of interest when, for instance in tobacco plants, it is desired t inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various diseases (e.g. fungus diseases). The inhibition of vegetative growth also makes closer planting possible in numerous crops, which means an increase in yield based on the area cropped.

B. Better yields both of plant parts and plant materials may be obtained with the active ingredients according to the invention. It is thus for instance possible to induce increased formation of buds, blossom, leaves, fruit, seed grains, roots and tubers, to increase the sugar content of sugar beets, sugarcane and citrus fruit, to raise the protein content of cereals and soybeans, and to stimulate the flow of latex in rubber trees.

The compounds according to the invention may raise the yield by influencing plant metabolism or by promoting or inhibiting vegetative and/or generative growth.

C. Finally, it is also possible with growth regulators to shorten or lengthen growth stages and to accelerate or retard the ripening process in plant parts either before or after harvesting.

A factor of economical interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also responsible for a chemically induced, readily controllable defoliation of plants.

The action of the compounds according to the invention is superior to that of prior art growth regulators. The action is manifested not only in monocotyledon crops, e.g., cereals such as wheat, barley, rye, oats and rice or Indian corn, but also in dicotyledons (e.g., sunflowers, tomatoes, soybeans, grapes, cotton and, particularly, rape) and various ornamentals such as chrysanthemums, poinsettias and hibiscus.

The new β-triazolyl oximes may be applied to the crop either by treating the seed, treating the soil, i.e., through the roots, or by spraying the leaves. Because the active ingredients are well tolerated by the crop plants, application rates may vary within a wide range.

When the active ingredients are used to treat seed, active ingredient amount of from 0.001 to 50 g, preferably from 0.01 to 10 g, per kg of seed are generally required.

When the active ingredients are applied to the soil or foliage, amounts of from 0.01 to 12 kg/ha, preferably from 0.25 to 3 kg/ha, are generally considered to be sufficient.

The compounds of the invention can be converted into the conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvents. Suitable auxiliaries are, essentially, solvents, for example aromatics, e.g. xylene and benzene; chloroaromatics, e.g. chlorobenzene, paraffins, e.g. petroleum fractions, alcohols, e.g. methanol and butanol, amines, e.g. ethanolamine, dimethylformamide, and water; solid carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The formulations in general contain from 0.1 to 95 percent by weight of active ingredient, preferably from 0.5 to 90 percent.

The formulations, and the ready-to-use preparations obtained therefrom, e.g., solutions, emulsions, suspensions, powders, dusts, pastes or granules, are applied in the conventional manner, e.g. preemergence, postemergence, or as seed dressing.

The above ready-to-use preparations may contain other active ingredients together with those according to the invention, e.g. herbicides, insecticides, other growth regulators and fungicides, or may be mixed with fertilizers and applied together with these. Mixtures with other growth regulators often broadens the spectrum of action. With a number of such growth regulator mixtures, synergistic effects also occur, i.e., the action of the combination product is greater than the sum of the actions of its individual components.

In the following examples, the action of the compounds to be used in accordance with the invention is demonstrated, without further possibilities of use as growth regulators being excluded.

The following examples illustrate the biological action of the new compounds.

I. Greenhouse experiments

The test plants were grown in plastic dishes 12.5 cm in diameter and containing peat substrate provided with sufficient nutrients. For the preemergence treatment, the compounds were applied as aqueous formulations in various concentrations to the seedbed on the day of sowing. For the leaf treatment, the plants were sprayed at a height of about 10 cm with aqueous formulations of the active ingredients in various concentrations. The growth-regulating action of the compounds examined was determined by measuring the plant height at the end of the experiment and comparing it with that of the untreated plants. The agents used for comparison purposes were the prior art active ingredients CCC (A) and 1-(4'-bromophenyl)-1-allyloxy-2-(1'',2'',4''-triazolyl-(1'')-ethane (B).

The results obtained are given in the tables below.
Comparative compounds:

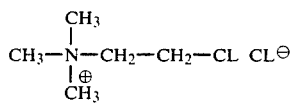
A

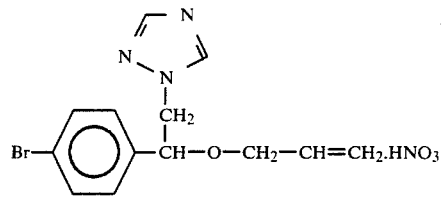
B

II. Vegetation experiments

Spring rape of the "Kosa" variety was grown in metal vessels in a neutral, loamy sand provided with sufficient nutrients.

For the soil treatment, the compounds were sprayed as aqueous formulations onto the seedbed on the day of sowing. For the leaf treatment, the plants were sprayed at a height of about 16 cm with aqueous formulations of the compounds.

The application rates were 5 and 10 mg of active ingredient per vessel. In each case, 4 vessels formed 1 variant. At the end of the experiment (ripeness) the height of the plants was measured and compared with the untreated plants.

III. Hydroponic cotton experiment

Cotton plants of the "Delta Pine" variety which had been grown in quartz sand were subjected to hydroponic treatment in 4-liter vessels; sufficient nutrient solution and trace elements were provided. The active ingredients were added to the nutrient solution at a plant height of about 13 cm. The plants were in continuous contact with the active ingredients. The growth height was measured after 46 days and compared with that of untreated plants.

EXAMPLE I.1

Influence on the height of spring barley of the "Union" variety

Preemergence treatment; duration of expt.: 19 days

| Active ingredient no. | Concentration in mg/vessel | Growth height cm | % |
|---|---|---|---|
| Control (untreated) | — | 26.3 | 100 |
| A | 3 | 25.0 | 95.1 |
|   | 12 | 22.0 | 83.7 |
| B | 3 | 25.0 | 95.1 |
|   | 12 | 22.0 | 83.7 |
| 1 | 3 | 24.0 | 91.3 |
|   | 12 | 21.0 | 79.9 |

EXAMPLE I.2

Influence on height of spring rape of the "Petronova" variety

Preemergence treatment; duration of expt.: 15 days

| Active ingredient no. | Concentration in mg/vessel | Growth height cm | % |
|---|---|---|---|
| Control (untreated) | — | 12.1 | 100 |
| A | 3 | 12.0 | 99.2 |
|   | 12 | 12.0 | 99.2 |
| B | 3 | 11.5 | 95.0 |
|   | 12 | 10.0 | 82.6 |
| 1 | 3 | 6.0 | 49.6 |
|   | 12 | 4.6 | 37.2 |

EXAMPLE I.3

Influence on height of spring rape of the "Petronova" variety

Leaf treatment; duration of expt.: 22 days

| Active ingredient no. | Concentration in mg/vessel | Growth height cm | % |
|---|---|---|---|
| Control (untreated) | — | 18.6 | 100 |
| A | 1.5 | 17.5 | 94.1 |
|   | 6 | 17.5 | 94.1 |
| B | 1.5 | 17.5 | 94.1 |
|   | 6 | 17.0 | 91.4 |
| 1 | 1.5 | 16.5 | 88.7 |
|   | 6 | 14.5 | 78.0 |

EXAMPLE I.4

Influence on height of spring rape of the "Petronova" variety

Preemergence treatment; duration of expt.: 16 days

| Active ingredient no. | Concentration in mg/vessel | Growth height cm | % |
|---|---|---|---|
| Control (untreated) | — | 13.5 | 100 |
| A | 3 | 13.0 | 96.3 |
|   | 12 | 12.5 | 92.6 |
| B | 3 | 12.5 | 92.6 |
|   | 12 | 11.0 | 81.5 |
| 11 | 3 | 9.0 | 66.7 |
|   | 12 | 6.5 | 48.2 |
| 15 | 3 | 10.0 | 74.1 |
|   | 12 | 8.0 | 59.3 |

EXAMPLE I.5

Influence on height of spring rape of the "Petronova" variety

Preemergence treatment; duration of expt.: 16 days

| Active ingredient no. | Concentration in mg/vessel | Growth height cm | % |
|---|---|---|---|
| Control (untreated) | — | 16.6 | 100 |
| A | 3 | 15.5 | 90.4 |
|   | 12 | 14.5 | 87.4 |
| B | 3 | 15.0 | 90.4 |
|   | 12 | 11.0 | 66.3 |
| 29 | 3 | 9.5 | 57.2 |
|   | 12 | 8.5 | 51.2 |

EXAMPLE I.6

Influence on height of soybeans of the "SRF 450" variety

Leaf treatment; duration of expt.: 40 days

| Active ingredient no. | Concentration in mg/vessel | Growth height cm | % |
|---|---|---|---|
| Control (untreated) | — | 28.9 | 100 |
| A | 1.5 | 28.0 | 96.9 |
|  | 6 | 28.0 | 96.9 |
| 3 | 1.5 | 26.0 | 90.0 |
|  | 6 | 24.0 | 83.0 |
| 11 | 1.5 | 25.0 | 86.5 |
|  | 6 | 17.0 | 58.8 |
| 14 | 1.5 | 27.0 | 93.4 |
|  | 6 | 24.0 | 83.0 |
| 15 | 1.5 | 24.0 | 83.0 |
|  | 6 | 17.0 | 58.8 |
| 20 | 1.5 | 25.0 | 86.5 |
|  | 6 | 24.0 | 83.0 |

EXAMPLE I.7

Influence on height of spring wheat of the "Kolibri" variety

Preemergence treatment; duration of expt.: 14 days

| Active ingredient no. | Concentration in mg/vessel | Growth height cm | % |
|---|---|---|---|
| Control (untreated) | — | 30.6 | 100 |
| A | 3 | 21.6 | 70.3 |
|  | 12 | 20.0 | 65.4 |
| 10 | 3 | 20.0 | 65.4 |
|  | 12 | 16.0 | 52.3 |

EXAMPLE I.8

Influence on height of spring rape of the "Kosa" variety

Preemergence treatment; duration of expt.: 16 days

| Active ingredient no. | Concentration in mg/vessel | Growth height cm | % |
|---|---|---|---|
| Control (untreated) | — | 15.3 | 100 |
| A | 3 | 14.0 | 91.5 |
|  | 12 | 14.0 | 91.5 |
| 10 | 3 | 13.0 | 85.0 |
|  | 12 | 9.5 | 62.1 |

EXAMPLE I.9

Influence on height of spring rape of the "Kosa" variety

Preemergence treatment; duration of expt.: 16 days

| Active ingredient no. | Concentration in mg/vessel | Growth height cm | % |
|---|---|---|---|
| Control (untreated) | — | 15.9 | 100 |
| A | 3 | 15.9 | 100 |
|  | 12 | 14.5 | 91.2 |
| 17 | 3 | 11.5 | 72.3 |
|  | 12 | 7.5 | 47.2 |

EXAMPLE I.10

Influence on height of spring rape of the "Kosa" variety

Leaf treatment; duration of expt.: 18 days

| Active ingredient no. | Concentration in mg/vessel | Growth height cm | % |
|---|---|---|---|
| Control (untreated) | — | 16.4 | 100 |
| A | 1.5 | 15.5 | 94.5 |
|  | 6 | 15.0 | 91.5 |
| 10 | 1.5 | 15.5 | 94.5 |
|  | 6 | 13.5 | 82.3 |

EXAMPLE I.11

Influence on height of spring rape of the "Kosa" variety

Leaf treatment; duration of expt.: 18 days

| Active ingredient no. | Concentration in mg/vessel | Growth height cm | % |
|---|---|---|---|
| Control (untreated) | — | 16.3 | 100 |
| A | 1.5 | 15.0 | 89.3 |
|  | 6 | 15.0 | 89.3 |
| 17 | 1.5 | 14.0 | 83.3 |
|  | 6 | 12.0 | 71.4 |

EXAMPLE II.1

Influence on height of spring rape of the "Kosa" variety

Preemergence treatment

| Active ingredient no. | Concentration in mg/vessel | Growth height cm | % |
|---|---|---|---|
| Control (untreated) | — | 108.7 | 100 |
| B | 5 | 99.7 | 91.7 |
|  | 10 | 93.3 | 85.8 |
| 1 | 5 | 68.5 | 63.0 |
|  | 10 | 54.0 | 49.7 |
| 11 | 5 | 72.9 | 67.1 |
|  | 10 | 60.6 | 55.8 |
| 15 | 5 | 98.0 | 90.2 |
|  | 10 | 91.0 | 83.7 |

EXAMPLE II.2

Influence on height of spring rape of the "Kosa" variety

Leaf treatment

| Active ingredient no. | Concentration in mg/vessel | Growth height cm | % |
|---|---|---|---|
| Control (untreated) | — | 106.3 | 100 |
| B | 5 | 102.0 | 96.0 |
|  | 10 | 97.0 | 91.3 |
| 1 | 5 | 85.5 | 80.4 |
|  | 10 | 75.0 | 70.6 |
| 11 | 5 | 89.0 | 83.7 |
|  | 10 | 77.0 | 72.4 |
| 15 | 5 | 94.0 | 88.4 |
|  | 10 | 86.0 | 80.9 |

EXAMPLE III.1

Influence on height of cotton of the "Delta Pine" variety (hydroponic treatment)

| Active ingredient no. | Concentration in mg/vessel | Growth height cm | % |
|---|---|---|---|
| Control (untreated) | — | 34.5 | 100 |

| Active ingredient no. | Concentration in mg/vessel | Growth height cm | % |
|---|---|---|---|
| 1 | 0.5 | 24.7 | 71.6 |
|   | 1.5 | 17.7 | 51.3 |
|   | 3.0 | 15.0 | 43.5 |

EXAMPLE 5

90 parts by weight of compound 1 is mixed with 10 parts by weight of N-methyl-α-pyrrolidone. A mixture is obtained which is suitable for application in the form of very fine drops.

EXAMPLE 6

20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE 8

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, spray liquor is obtained containing 0.1% by weight of the active ingredient.

EXAMPLE 10

3 parts by weight of compound 3 is intimately mixed with 97 parts by weight of particulate kaolin. A dust is obtained containing 3% by weight of the active ingredient.

EXAMPLE 11

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 12

40 parts by weight of compound 1 is intimately mixed with 10 parts of the sodium salt of a phenolsulfonic acid-urea-formaldehyde condensate, 2 parts of silica gel and 48 parts of water to give a stable, aqueous dispersion. Dilution in 100,000 parts by weight of water gives an aqueous dispersion containing 0.04 wt% of active ingredient.

EXAMPLE 13

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. 3-(1',2',4'-triazolyl-(1'))-1-(4''-bromophenyl)-4,4-dimethylpentan-1-one-O-acetyl oxime, and 3-(1',2',4'-triazolyl-(1'))-1-(4''-bromophenyl)-4,4-dimethylpentan-1-one-O-propionyl oxime.

2. A process for influencing plant growth, wherein crop plants or the soil in which the crop plants are grown are treated with a β-triazolyl oxime of the formula $$R^1-\overset{N-O-R^3}{\underset{}{C}}-CH_2-CH-R^2 \quad \underset{N}{\overset{N}{\underset{N}{\diagdown}}}\diagup \quad I$$

wherein $R^1$ and $R^2$ are identical or different and each denotes alkyl of 1 to 6 carbon atoms, furanyl, thiophenyl, naphthyl, biphenyl or phenyl, phenyl being unsubstituted or substituted by fluoro, chloro, bromo, alkyl of 1 to 4 carbon atoms, trifluoromethyl, nitro, or by alkoxy of 1 to 4 carbon atoms, and $R^3$ denotes alkyl of 1 to 4 carbon atoms, alkenyl of 1 to 4 carbon atoms, benzyl, —CO—$R^4$, $R^4$ denoting alkyl of 1 to 4 carbon atoms which is unsubstituted or halogen- or alkoxy-substituted, or $R^3$ denotes —CO—NH—$R^5$, $R^5$ denoting alkyl of 1 to 4 carbon atoms or phenyl which is substituted by chlorine.

* * * * *

UNITED STATES PATENT AND TRADEMARK OFFICE
CERTIFICATE OF CORRECTION

PATENT NO. : 4,684,392
DATED : Aug. 4, 1987
INVENTOR(S) : Rentzea et al.

It is certified that error appears in the above-identified patent and that said Letters Patent are hereby corrected as shown below:

Col. 22, before line 33 insert -- A $\beta$-triazolyl oxime selected from the group consisting of --

Signed and Sealed this

First Day of December, 1987

Attest:

DONALD J. QUIGG

*Attesting Officer*    *Commissioner of Patents and Trademarks*